(12) United States Patent  (10) Patent No.: US 9,333,051 B2
Li et al.  (45) Date of Patent: May 10, 2016

(54) METHOD FOR MANUFACTURING APPLIANCES FOR REPOSITIONING TEETH

(75) Inventors: Zhongke Li, Xi'an (CN); Jie Tian, Shanghai (CN)

(73) Assignee: WUXI EA MEDICAL INSTRUMENTS TECHNOLOGIES LIMITED, Shanghai (CN)

( * ) Notice: Subject to any disclaimer, the term of this patent is extended or adjusted under 35 U.S.C. 154(b) by 616 days.

(21) Appl. No.: 13/410,292

(22) Filed: Mar. 2, 2012

(65) Prior Publication Data

US 2013/0103175 A1 Apr. 25, 2013

(51) Int. Cl.
  *G06F 19/00* (2011.01)
  *A61C 7/00* (2006.01)
  *G06F 17/10* (2006.01)
  *G06F 17/50* (2006.01)
  *A61B 5/00* (2006.01)

(52) U.S. Cl.
  CPC .............. *A61C 7/002* (2013.01); *G06F 17/10* (2013.01); *A61B 5/4547* (2013.01); *G05B 2219/45167* (2013.01); *G06F 17/50* (2013.01); *G06F 19/3437* (2013.01)

(58) Field of Classification Search
  CPC ............ A61C 7/002; A61C 7/00; A61B 6/14; A61B 19/50
  See application file for complete search history.

(56) References Cited

U.S. PATENT DOCUMENTS

| 7,916,911 | B2 * | 3/2011 | Kaza et al. | 382/128 |
| 8,591,225 | B2 * | 11/2013 | Wu et al. | 433/24 |
| 8,636,510 | B2 * | 1/2014 | Kitching et al. | 433/24 |
| 2006/0286501 | A1 * | 12/2006 | Chishti et al. | 433/24 |
| 2007/0003907 | A1 * | 1/2007 | Chishti et al. | 433/217.1 |
| 2007/0141527 | A1 * | 6/2007 | Kuo et al. | 433/24 |
| 2008/0248443 | A1 * | 10/2008 | Chishti et al. | 433/24 |
| 2008/0280247 | A1 * | 11/2008 | Sachdeva et al. | 433/24 |
| 2008/0305451 | A1 * | 12/2008 | Kitching et al. | 433/24 |
| 2008/0305452 | A1 * | 12/2008 | Sterental et al. | 433/24 |

(Continued)

OTHER PUBLICATIONS

Hicks et al., Heuristic reasoning and cognitive biases: Are they hindrances to judgments and decision making in orthodontics?, American Association of Orthodontics, Apr. 2010.*

(Continued)

*Primary Examiner* — Darrin Dunn
(74) *Attorney, Agent, or Firm* — Jun He Law Offices P.C.; James J. Zhu (57) ABSTRACT

A method for generating digital data sets is provided. The method includes: obtaining a first digital data set representing a first tooth arrangement; providing at least one operator for modifying a digital data set representing a tooth arrangement; providing target data which represents orthodontic treatment requirements; generating a second digital data set representing a second tooth arrangement based on the first digital data set using a state space search method and the at least one operator; determining whether the second tooth arrangement meets the treatment requirements; generating a $N^{th}$ digital data set representing a $N^{th}$ tooth arrangement based on a $N-1^{th}$ data set representing a $N-1^{th}$ tooth arrangement using the state space search method and the at least one operator, where N is an integer greater than 2; and determining whether the $N^{th}$ tooth arrangement meets the treatment requirements.

8 Claims, 6 Drawing Sheets

(56) References Cited

U.S. PATENT DOCUMENTS

| | | | |
|---|---|---|---|
| 2008/0305453 A1* | 12/2008 | Kitching et al. | 433/24 |
| 2008/0306724 A1* | 12/2008 | Kitching et al. | 704/2 |
| 2009/0042168 A1* | 2/2009 | Luo et al. | 433/215 |
| 2009/0191502 A1* | 7/2009 | Cao et al. | 433/24 |
| 2009/0246726 A1* | 10/2009 | Chelnokov et al. | 433/24 |
| 2009/0291417 A1* | 11/2009 | Rubbert et al. | 433/215 |
| 2009/0316966 A1* | 12/2009 | Marshall et al. | 382/128 |
| 2010/0105009 A1* | 4/2010 | Karkar et al. | 433/215 |
| 2010/0129763 A1* | 5/2010 | Kuo | 433/6 |
| 2010/0151404 A1* | 6/2010 | Wu et al. | 433/24 |
| 2010/0151405 A1* | 6/2010 | Marshall | 433/24 |
| 2010/0159413 A1* | 6/2010 | Kuo | 433/24 |
| 2010/0167243 A1* | 7/2010 | Spiridonov et al. | 433/224 |
| 2010/0260405 A1* | 10/2010 | Cinader, Jr. | 382/131 |
| 2010/0280798 A1* | 11/2010 | Pattijn et al. | 703/1 |
| 2011/0159451 A1* | 6/2011 | Kuo et al. | 433/24 |
| 2011/0212420 A1* | 9/2011 | Vuillemot | 433/215 |
| 2011/0295402 A1* | 12/2011 | Dumitrescu et al. | 700/98 |
| 2012/0035901 A1* | 2/2012 | Kitching et al. | 703/11 |
| 2012/0099778 A1* | 4/2012 | Helm et al. | 382/132 |
| 2013/0029283 A1* | 1/2013 | Matty | 433/3 |
| 2013/0089828 A1* | 4/2013 | Borovinskih et al. | 433/6 |
| 2013/0110469 A1* | 5/2013 | Kopelman | 703/1 |
| 2014/0087323 A1* | 3/2014 | Kaza et al. | 433/6 |
| 2014/0120490 A1* | 5/2014 | Borovinskih et al. | 433/6 |
| 2014/0229145 A1* | 8/2014 | Van Lierde et al. | 703/1 |

OTHER PUBLICATIONS

Lin et al., Advances in Computer Science, Environment, Ecoinformatics, and Education, Int. National Conf, Wuhan, China, Aug. 2011, Proceedings, Part 1.*

Bartsch, Patterns and prediction of orthodontic treatment course, The European Journal of Orthodontics, Jan. 1997.*

* cited by examiner

METHOD FOR MANUFACTURING APPLIANCES FOR REPOSITIONING TEETH

CROSS-REFERENCE TO RELATED APPLICATIONS

This application claims priority from Chinese Patent Application Serial Number: 201110322561.X filed Oct. 21, 2011, which is incorporated herein by reference in its entirety.

FIELD OF THE APPLICATION

The present application is related to orthodontic treatment, especially related to computer aided methods for providing appliances for repositioning teeth.

BACKGROUND

Conventionally, repositioning teeth is accomplished by wearing bands and braces, and using archwires, springs, and O-rings etc. The drawbacks of the conventional methods include poor appearance and comfort, and difficulty to maintain dental hygiene. In addition, a long term training is required before a clinician could practice the conventional methods. Furthermore, in conventional methods, a clinician needs to spend much time on adjusting the appliances during each patient visit, and this makes the treatment complicated. Compared with conventional appliances, an invisible orthodontic treatment does not require brackets and archwires, instead it uses a series of invisible appliances made of safe elastic transparent polymer materials. Therefore, the invisible orthodontic treatment is almost unnoticeable, and will not affect life quality. Meanwhile, since brackets and archwires are not required, clinical operation is greatly simplified, and much time and labor could be saved. Because of the above mentioned advantages, invisible orthodontic treatment is more and more popular.

Invisible appliances arise from the combination of computer aided method, rapid prototyping, and new materials. An invisible appliance is transparent, could be put on and taken off by the patient himself. Like conventional appliances, an invisible appliance also moves teeth by exerting proper and controlled forces on teeth. A practitioner may simulate the treatment on a computer, and may make an appliance using medical elastic transparent polymer materials for each stage of the treatment. In an invisible orthodontic treatment, a patient uses a series of invisible appliances in a predetermined order. When a patient wears an invisible appliance, he/her will feel load of forces on teeth, which will move the teeth toward an arrangement for which the appliance is designed. Having worn an appliance for a certain period of time, the patient may take off the current appliance, and put on a next appliance, and so on, until the teeth are moved from the original mal-aligned arrangement to an aligned arrangement gradually.

An invisible appliance may be made by manually modifying a positive plaster model of teeth, and then forming on the positive model the invisible appliance. However, this method has the drawbacks such as low precision, and low efficiency. An invisible appliance may also be made by first providing a digital data set representing a modified teeth arrangement, producing a positive model of the modified teeth arrangement by laser rapid prototyping, and forming on the positive model the invisible appliance. Conventional computer aided methods for manufacturing invisible appliances generate a plurality of intermediate teeth arrangements based on an original teeth arrangement and a final teeth arrangement using an interpolation algorithm. Once the final teeth arrangement is determined, the plurality of intermediate teeth arrangements are determined accordingly, therefore it is difficult to adjust or fine-tune the treatment between teeth during the treatment, and it is also difficult to set steps for corresponding operations on a same tooth separately. According to the above, a flexible method for designing and providing invisible appliances is needed.

SUMMARY

In one aspect, the present application provides a method for generating digital data sets representing corresponding tooth arrangements using a state space search method. The method includes: obtaining a first digital data set representing a first tooth arrangement; providing at least one operator for modifying a digital data set representing a tooth arrangement; and generating a second digital data set representing a second tooth arrangement based on the first digital data set using the state space search method and the at least one operator.

In some embodiments, a tooth arrangement may be an arrangement of one of an upper jaw or a low jaw of a patient. In some embodiments, a tooth arrangement may be an arrangement of a part of the upper jaw or the low jaw. In some embodiments, a tooth arrangement may be an arrangement of both the upper jaw and the lower jaw. In some embodiments, a tooth arrangement may be an arrangement of a part of both the upper jaw and the low jaw. In some embodiments, a tooth arrangement may include a single tooth. In some embodiments, a tooth arrangement may include a plurality of teeth.

A state space search method translates the process of solving a problem into a process of finding a path from an original state to a target state in a state space. For a state space search method, we may give [S, O, G], wherein S represents a set of original states, O represents a set of operators, and G represents a set of target states. When an operator is applied on the current state, the current state will be modified to generate a new state.

Each time an operator is applied, a new state will be generated. A state diagram includes all states, some of which are target states. The problem is solved as long as a path from an original state to a target state is found, and the solution is application of a series of operators. In some cases, a shortest path from the original state to a target state may be an optimal solution.

State space search methods include depth first methods and breadth first methods. A breadth first method begins at the root node, and explores all the neighboring nodes. Then for each of those nearest nodes, it explores their unexplored neighbor nodes, and so on, until it finds a target node. A depth first search method starts at the root node and explores as far as possible along each branch before backtracking. Breadth first search methods and depth first search methods are blind search methods. State space search methods further include heuristic search methods.

A heuristic search method evaluates each node on a same level to find out the best one, and explores from the best node, and so on, until a target node is found. This can improve the efficiency of the search.

A heuristic search method evaluates a node using a cost function, and the cost function may be written as:

$$f(n)=g(n)+h(n) \qquad \text{equation (1)}$$

where f(n) represents the cost function of a node n, g(n) represents the actual cost of reaching the node n from the root node, h(n) represents an estimated cost of reaching a target node from the node n by an optimal path. h(n) represents heuristic information. g(n) is known and presents the trend of breadth first search. When h(n)>>g(n), g(n) may be neglected, and the efficiency can be improved. In practice, for each new generated node, a value of the cost function is calculated. The node having the minimum value may be selected as the best node, and the search may continue from the selected node, and so on, until a target node is found.

State space search methods can be used to make orthodontic treatment plan. In this case, an original state may be an original tooth arrangement of a patient, operators may include one of non-operation, extraction of tooth, interproximal enamel reduction, movement, and rotation etc., and target nodes may be tooth arrangements that meet the requirements given by a clinician.

In the environment of using a state space search method to make an orthodontic treatment plan, in most cases, node, state, and digital data set may be interchanged.

An operator is a discrete computing operation. When an operator is applied on a tooth, a computer will correspondingly modify the current digital data set representing the current tooth arrangement, and the modified digital data set represents a new tooth arrangement which may be obtained by applying a corresponding operation on the tooth based on the current tooth arrangement. For example, when an operator corresponding to movement along the positive x-axis by 1 mm is applied on a tooth, the computer will modify the digital data set representing the current tooth arrangement, and the modified digital data set represents a tooth arrangement which may be obtained by moving the tooth along the positive x-axis by 1 mm based on the current tooth arrangement.

In some embodiments, operators include at least one of the following: movement along positive x-axis, movement along negative x-axis, movement along positive y-axis, movement along negative y-axis, movement along positive z-axis, movement along negative z-axis, clockwise rotation about x-axis, counterclockwise rotation about x-axis, clockwise rotation about y-axis, counterclockwise rotation about y-axis, clockwise rotation about z-axis, counterclockwise rotation about z-axis, and any combination of the above.

In some embodiments, operators may include interproximal enamel reduction. In some embodiments, interproximal enamel reduction may be limited. For example, 0.05~0.5 mm for upper incisors, 0.05~0.8 mm for upper posterior teeth, 0.05~0.5 mm for lower incisors, 0.05~0.8 mm for lower posterior teeth. Those skilled in the art will appreciate that the ranges may be adjusted according to the specific situation of a patient.

In some embodiments, the above method may further includes: providing target data; and determining whether the second digital data set matches the target data to determine whether the second tooth arrangement meets the orthodontic treatment requirement(s) represented by the target data.

In some embodiments, target data may include a predetermined range or a predetermined value of at least one of the following parameters: dental arch, the amount of crowding, overjet, overbite, dental arch convexity, depth of curve of Spee, Bolton ratio, dental arch width, arch symmetry, angulation of crown, tongue, and midline.

In case of target data including a predetermined range of a parameter, a tooth arrangement meets the requirement on the parameter as long as the value of the parameter of the tooth arrangement falls in the range.

In case of target data including a predetermined value of a parameter, a tooth arrangement meets the requirement on the parameter as long as the value of the parameter of the tooth arrangement equals to the predetermined value.

1. The amount of crowding $a_n$: The amount of crowding is defined as the differences between the sum of crown width and the actual arch length. A negative value indicates space deficiency. A positive value indicates space excess. There is no crowding or space if the value is zero. The crown width refers to the mesio-distal width of the crown. The actual lower arch length is obtained by measuring arch form arc. The arch form arc starts from the mesial contact point of one side first molar, crossing the contact points of premolars, cusps of canines, edge of incisors, and ends at the other mesial contact point of first molar. If all the lower incisors inclined labially or lingually, the arc should be on the alveolar ridge. The same goes for the measurement of actual upper arch length. In a normal tooth arrangement, the amount of crowding should be zero. However, a range may be set for a specific patient, and if the amount of crowding falls in the range, the tooth arrangement meets the requirement on this parameter.

2. Overjet $b_n$: Overjet is defined as the distance between the upper incisor edge and the labial surface of the lower central incisor. A normal overjet is usually from about 2 mm to about 4 mm.

3. Overbite $c_n$: Overbite refers to the extent of vertical overlap of the maxillary central incisors over the mandibular central incisors. It is the distance from the edge point of lower central incisor to the foot of perpendicular of upper central incisor edge point to the labial surface of lower central incisor. In a normal tooth arrangement, overbite should be less than ⅓ height of the crown of the lower incisors.

4. Depth of curve of Spec $d_n$: The depth of curve of Spec is defined as the distance from the vertex of the curve to the plane consisted of incisor edge and the distal-most molar cusps. Generally, the normal depth of curve of Spee is about 2 mm. To level the curve of Spee, space is needed. The space needed is calculated as follows: to measure the depth of curve of Spee of both sides separately, the mean value is the space needed to level the curve of Spec.

5. Bolton ratio $e_n$: Bolton ratio reflects the relationship of mesio-distal width of upper and lower six anterior teeth and 12 upper and lower teeth (second and third molars excluded). Bolton ratio determines if there is discrepancy in upper and lower teeth width.

Anterior ratio=Sum $mand_6$/Sum $max_6$*100%
Overal ratio=Sum $mand_{12}$/Sum $max_{12}$*100%
The normal value from Bolton (Bolton,1958) are:
Anterior ratio: (77.2±0.22)%
Overall ratio: (91.3±0.26)%
The normal value of Chinese:
Anterior ratio: (78.8±1.72)%
Overall ratio: (91.5±1.51)%

According to the above ratios, the discrepancy can be determined whether in upper arch or in lower arch, in width of anterior teeth or posterior teeth.

6. Arch symmetry $f_n$: Draw a line along mid-palatal raphe as a reference midline. By measuring the distance to the midline of the same teeth on both sides, the symmetry of the arch can be determined. If the same teeth on both sides are not on the same plane in the anterior-posterior direction, it indicates that the tooth on one side is moved mesially.

7. Angulation of crown $g_n$: Angulation crown is defined as the angle between the long axis of clinical crown and the line perpendicular to the occlusal plane. If the gingival side of the long axis of clinical crown tilts distally, the value is defined as positive, otherwise, is defined as negative. In most cases, the value is positive in normal occlusion. In some embodiments, normal angulation of crown of each tooth are listed in the below table.

| Teeth in Upper Jaw | Angulation of Crown | Teeth in Lower Jaw | Angulation of Crown |
|---|---|---|---|
| 11, 21 | 5° | 31, 41 | 2° |
| 12, 22 | 9° | 32, 42 | 2° |
| 13, 33 | 11° | 33, 43 | 5° |
| 14, 24 | 2° | 34, 44 | 2° |
| 15, 25 | 2° | 35, 45 | 2° |
| 16, 26 | 0° | 36, 46 | 0° |
| 17, 27 | 0° | 37, 47 | 0° |

8. Tongue $h_n$: Tongue defines the angle between the tangent of clinical crown and a line perpendicular to the occlusal plane. If the gingival area of the crown is more toward the lingual, the result is a positive value, otherwise, the result is negative. In some embodiments, normal tongue of each tooth are listed in the below table.

| Teeth in Upper Jaw | Tongue | Teeth in Lower Jaw | Tongue |
|---|---|---|---|
| 11, 21 | 7° | 31, 41 | −1° |
| 12, 22 | 3° | 32, 42 | −1° |
| 13, 33 | −7° | 33, 43 | −11° |
| 14, 24 | −7° | 34, 44 | −17° |
| 15, 25 | −7° | 35, 45 | −22° |
| 16, 26 | −9° | 36, 46 | −25° |
| 17, 27 | −9° | 37, 47 | −25° |

9. Midline $i_n$: Midline is a phantom line which passes through the center of upper and lower central incisors. If the two lines coincide, it indicates that the midline of upper and lower arch is coordinating. If the two lines do not coincide, the difference between them is the value of midline deviation.

10. Dental arch convexity $j_n$: Generally, the position of lower incisor represents the dental arch convexity. It can be obtained by cephalometric analysis. To decrease dental arch convexity, space is needed, to increase dental arch convexity, space is created.

11. Dental arch width $k_n$: Generally, dental arch widths are measured in three sections, they are width between canines, width between bicuspids, and width between molars, respectively.

(1) Width between canines: This represents the width of anterior region of dental arch. It can be obtained by measuring the distance between the cusps of canines.

(2) Width between bicuspids: This represents the width of mid-region of dental arch. It can be obtained by measuring the distance between the central fossa of first bicuspids.

(3) Width between molars: This represents the width of posterior region of dental arch. It can be obtained by measuring the distance between the central fossa of first molars.

In some embodiments, the above method may further includes: generating a $N^{th}$ digital data set representing a $N^{th}$ tooth arrangement based on a $N-1^{th}$ digital data set representing a $N-1^{th}$ tooth arrangement using the state space search method and the at least one operator, where N is an integer greater than 2; and determining whether the $N^{th}$ digital data set matches the target data to determine whether the $N^{th}$ tooth arrangement meets the orthodontic treatment requirement(s). In some embodiments, each digital data set is generated based on the previous digital data set.

In some embodiments, the above method may further include: if the $N^{th}$ tooth arrangement meets the orthodontic treatment requirement(s) which means that the $N^{th}$ tooth arrangement is a desired tooth arrangement, forming a first digital data set sequence having a plurality of successive digital data sets from the second digital data set to the $N^{th}$ digital data set. The first digital data set sequence represents an orthodontic treatment plan or path. In some embodiments, a desired tooth arrangement meets the requirement(s) determined by a clinician based on the situation of a patient.

In some embodiments, N may be an integer greater than 2 and smaller than 50. For example, N may be 3, 4, 5, 6, 7, 8, 9, 10, 15, 20, 25, 30, 35, and 40 etc. In some embodiments, N may be greater than 50 but less than 100 (e.g., 50, 60, 70, 80, 90). N may be determined based on the situation of a patient.

In some embodiments, the above method may further include: selecting teeth that need to be repositioned to narrow the search space and to improve the efficiency of the search.

In some embodiments, the above method may further include: selecting at least one operator for at least one tooth, thus the unselected operators may not be applied on the tooth to narrow the search space, and to improve the efficiency of the search. In some embodiments, a plurality of operators may be selected for a tooth. For example, an operator corresponding to movement along positive x-axis and an operator corresponding to rotation clockwise about y-axis may be selected for a tooth. In some embodiments, two or more operators may be applied on a tooth at the same time. In some embodiments, only one operator may be applied on a tooth each time.

In some embodiments, the above method may further include: setting a limitation for at least one operator for at least one tooth. For example, a limitation of 2 mm may be set for an operator corresponding to movement along positive x-axis for a first tooth, and the movement of the first tooth along positive x-axis shall not exceed 2 mm. This may narrow the search space, and improve the efficiency of the search.

In some embodiments, the above method may further include: setting an order of tooth reposition. For example, an order may be set such that a $1^{st}$ tooth and a $12^{th}$ tooth will be repositioned synchronously first, and then a $3^{rd}$ and an $8^{th}$ tooth will be repositioned synchronously. This may also narrow the search space to improve the efficiency of the search.

In some embodiments, the above method may further include: setting a step for at least one operator for at least one tooth. For example, a step of an operator of movement may be set as a value in the range of 0.05~2 mm, such as 0.05 mm, 0.1 mm, 0.2 mm, 0.3 mm, 0.4 mm, 0.5 mm, 1 mm, 1.5 mm, and 2 mm etc. Preferably, a step of an operator of movement may be set as a value in the range of 0.2~0.3 mm, such as 0.2 mm, 0.25 mm, and 0.3 mm etc. For example, a step of an operator of rotation may be set as a value in the range of 0.05~5°, such as 0.05°, 0.1°, 0.15°, 0.2°, 0.3°, 0.4°, 0.5°, 1°, 1.5°, 2°, 2.5°, 3°, 3.5°, 4°, 4.5°, and 5° etc. Preferably, a step of an operator of rotation may be set as a value in the range of 1~3°, such as 1°, 1.5°, 2°, 2.5°, and 3° etc. In some embodiments, different steps may be set for a same operator for different teeth, respectively.

In some embodiments, the state space search method may be a heuristic search method, and the above method may further include: providing a cost function on which the heuristic search method is based.

In some embodiments, the cost function may include at least one of the following parameters: dental arch, the amount of crowding, overjet, overbite, dental arch convexity, depth of curve of Spee, Bolton ratio, dental arch width, arch symmetry, angulation of crown, tongue, and midline.

In some embodiments, the above method for generating digital data set may be conducted for a single tooth i.e. only one tooth needs to be adjusted. In some embodiments, the above method for generating digital data set may be conducted for a plurality of teeth of a patient. In some embodiments, the above method for generating digital data set may be conducted for all teeth of a patient.

In another aspect of the present application, a method for manufacturing appliances for repositioning tooth is provided. The method includes: producing a positive model of a tooth arrangement using a corresponding digital data set in the first digital data set sequence; and forming a negative model on the positive model as an appliance for repositioning tooth. In some embodiments, the negative model can be made by polymer films, such as elasticized acrylic.

In another aspect of the present application, a method for manufacturing appliances for repositioning tooth is provided. The method includes: producing a first series of successive positive models using the first digital data set sequence; and forming on the first series of positive models a first series of successive negative models as a set of successive appliances for repositioning tooth.

In another aspect of the present application, a method for manufacturing appliances for repositioning tooth is provided. The method includes: producing a plurality of positive models using a plurality of digital data sets selected from the first digital data set sequence; and forming on the plurality of positive models a plurality of negative models as appliances for repositioning tooth.

In some embodiments, a negative model may be directly manufactured on a numerical controlled machine tool using a corresponding digital data set, and the negative may be used as an appliance for repositioning tooth.

In some embodiments, the target data may be used to guide the state space search. For example, if a tooth arrangement is closer to the treatment requirements after an operator is applied on a tooth, then the operator may be applied on the tooth again to generate a next node, otherwise, in generation of the next node, the operator may not be applied on the tooth anymore.

In some embodiments, the orthodontic treatment may be divided into a plurality of segments. For example, in a first segment, a first digital data set sequence having a plurality of successive digital data sets from the first digital data set to a first desired digital data set may be generated, and a first plurality of appliances may be manufactured using a plurality of digital data sets foremost in the first digital data set sequence. In a second segment, related parameters of the state space search may be adjusted according to the use of the plurality of appliances to generate a second digital data set sequence based on the current tooth arrangement and the adjusted parameters. For example, one may re-select teeth need to be repositioned, or modify the steps of the operators, or may modify the target data, or the order of teeth reposition etc. A second plurality of appliances may be manufactured using a plurality of digital data sets foremost in the second digital data set sequence, and so on, until the teeth are aligned. This could provide a better treatment.

In another aspect of the present application, a computer readable medium is provided. The computer readable medium has a computer program stored therein, which program when executed by a computer may instruct the computer to conduct a method for generating digital data sets. The method includes: obtaining a first digital data set representing a first tooth arrangement; providing at least one operator for modifying a digital data set representing a tooth arrangement; and generating a second digital data set representing a second tooth arrangement based on the first digital data set using a state space search method and the at least one operator.

In some embodiments, the above method may further includes: providing target data; and determining whether the second digital data set matches the target data to determine whether the second tooth arrangement meets the orthodontic treatment requirement(s) represented by the target data.

In some embodiments, the above method may further includes: generating a $N^{th}$ digital data set representing a $N^{th}$ tooth arrangement based on a $N-1^{th}$ digital data set representing a $N-1^{th}$ tooth arrangement using the state space search method and the at least one operator, where N is an integer greater than 2; and determining whether the $N^{th}$ digital data set matches the target data to determine whether the $N^{th}$ tooth arrangement meets the orthodontic treatment requirement(s).

In some embodiments, the above method may further include: if the $N^{th}$ tooth arrangement meets the orthodontic treatment requirement(s) which means that the $N^{th}$ tooth arrangement is a desired tooth arrangement, forming a first digital data set sequence having a plurality of digital data sets from the second digital data set to the $N^{th}$ digital data set.

In another aspect of the present application, a computer system for generating digital data sets representing tooth arrangements is provided. The computer system includes a processor and a storage device having a computer program stored therein, which program when executed by the processor may instruct the computer to conduct a method for generating digital data sets. The method includes: obtaining a first digital data set representing a first tooth arrangement; providing at least one operator for modifying a digital data set representing a tooth arrangement; and generating a second digital data set representing a second tooth arrangement based on the first digital data set using a state space search method and the at least one operator.

In some embodiments, the above method may further includes: providing target data; and determining whether the second digital data set matches the target data to determine whether the second tooth arrangement meets the orthodontic treatment requirement(s) represented by the target data.

In some embodiments, the above method may further includes: generating a $N^{th}$ digital data set representing a $N^{th}$ tooth arrangement based on a $N-1^{th}$ digital data set representing a $N-1^{th}$ tooth arrangement using the state space search method and the at least one operator, where N is an integer greater than 2; and determining whether the $N^{th}$ digital data set matches the target data to determine whether the $N^{th}$ tooth arrangement meets the orthodontic treatment requirement(s).

In some embodiments, the above method may further include: if the $N^{th}$ tooth arrangement meets the orthodontic treatment requirement(s) which means that the $N^{th}$ tooth arrangement is a desired tooth arrangement, forming a first digital data set sequence having a plurality of digital data sets from the second digital data set to the $N^{th}$ digital data set.

In some embodiments, if there is interference between teeth in a tooth arrangement, a digital data set representing the tooth arrangement may not be used to generate subsequent digital data sets, thus to avoid interference between teeth during a treatment.

In some embodiments, during a tooth reposition treatment, an intermediate tooth arrangement (between $1^{st}$ and Nth) during the treatment may be treated as a first tooth arrangement so that follow-on search and data sets can be made on the basis of the intermediate arrangement. This is useful for a clinician to observe the treatment process and intervene the process whenever necessary.

Compared with conventional methods, the present application is more flexible, may better customize orthodontic treatment to better fit various situations.

DETAILED DESCRIPTION OF ILLUSTRATED EMBODIMENTS

In some embodiments, a heuristic state space search method may be used. The cost function of the heuristic state space search method may include but not limited to the following parameters: the amount of crowding, overjet, overbite, dental arch convexity, depth of curve of Spee, Bolton ratio, dental arch width, arch symmetry, angulation of crown, tongue, and midline.

In some embodiments, in a heuristic state space search method, a weight may be given for each parameter, and the cost function may be re-written as:

$$f(n) = \{a_n*w_a, b_n*w_b, e_n*w_c, d_n*w_d, e_n*w_e, f_n*w_f, g_n*w_g, h_n*w_h, i_n*w_i\}$$

In some embodiments, a threshold G may be given, and the value of f(n) of a node n may be compared with G to determine whether node n is good enough.

Various predetermined values may be determined by a clinician based on the situation of a patient.

In one embodiment, a patient's upper and lower jaws are scanned, and each tooth needs to be repositioned is given a coordinate (x, y, z). Each operator of movement is given a step of 0.2 mm, and each operator of rotation is given a step of 1°. For one tooth, there are 729 combinations based on the above mentioned operators:

(x11, y11, z11), x11 represents an operation of moving δ (δ=0.2 mm) along positive x-axis and rotating ω (ω=1°) clockwise about x-axis, y11 represents an operation of moving δ (δ=0.2 mm) along positive y-axis and rotating ω (ω=1° clockwise about y-axis, z11 represents an operation of moving δ (δ=0.2 mm) along positive z-axis and rotating ω (ω=1° clockwise about z-axis;

(x12, y11, z11), x12 represents an operation of moving δ (δ=0.2 mm) along positive x-axis and no rotating about x-axis, y11 represents an operation of moving δ (δ=0.2 mm) along positive y-axis and rotating ω (ω=1° clockwise about y-axis, z11 represents an operation of moving δ (δ=0.2 mm) along positive z-axis and rotating ω (ω=1°) clockwise about z-axis;

(x13, y11, z11), x13 represents an operation of moving δ (δ=0.2 mm) along positive x-axis and rotating ω (ω=1° counterclockwise about x-axis, y11 represents an operation of moving δ (δ=0.2 mm) along positive y-axis and rotating ω (ω=1°) clockwise about y-axis, z11 represents an operation of moving δ (δ=0.2 mm) along positive z-axis and rotating ω (ω=1° clockwise about z-axis;

(x21, y11, z11), x21 represents an operation of no moving along x-axis and rotating ω (ω=1° clockwise about x-axis, y11 represents an operation of moving δ (δ=0.2 mm) along positive y-axis and rotating ω (ω=1° clockwise about y-axis, z11 represents an operation of moving δ (δ=0.2 mm) along positive z-axis and rotating ω (ω=1°) clockwise about z-axis;

(x22, y11, z11), x22 represents an operation of no moving along x-axis and no rotating about x-axis, y11 represents an operation of moving δ (δ=0.2 mm) along positive y-axis and rotating ω (ω=1° clockwise about y-axis, z11 represents an operation of moving δ (δ=0.2 mm) along positive z-axis and rotating ω (ω=1° clockwise about z-axis;

(x23, y11, z11), x23 represents an operation of no moving along x-axis and rotating ω (ω=1° counterclockwise about x-axis, y11 represents an operation of moving δ (δ=0.2 mm) along positive y-axis and rotating ω (ω=1°) clockwise about y-axis, z11 represents an operation of moving δ (δ=0.2 mm) along positive z-axis and rotating ω (ω=1°) clockwise about z-axis;

(x31, y11, z11), x31 represents an operation of moving δ (δ=0.2 mm) along negative x-axis and rotating ω (ω=1°) clockwise about x-axis, y11 represents an operation of moving δ (δ=0.2 mm) along positive y-axis and rotating ω (ω=1° clockwise about y-axis, z11 represents an operation of moving δ (δ=0.2 mm) along positive z-axis and rotating ω (ω=1°) clockwise about z-axis;

(x32, y11, z11), x32 represents an operation of moving δ (δ=0.2 mm) along negative x-axis and no rotating about x-axis, y11 represents an operation of moving δ (δ=0.2 mm) along positive y-axis and rotating ω (ω=1° clockwise about y-axis, z11 represents an operation of moving δ (δ=0.2 mm) along positive z-axis and rotating ω (ω=1°) clockwise about z-axis;

(x33, y11, z11), x33 represents an operation of moving δ (δ=0.2 mm) along negative x-axis and rotating ω (ω=1° counterclockwise about x-axis, y11 represents an operation of moving δ (δ=0.2 mm) along positive y-axis and rotating ω (ω=1°) clockwise about y-axis, z11 represents an operation of moving 3 (6=0.2 mm) along positive z-axis and rotating ω (ω=1° clockwise about z-axis;

(x11, y12, z11), x11 represents an operation of moving δ (δ=0.2 mm) along positive x-axis and rotating ω (ω=1° clockwise about x-axis, y12 represents an operation of moving δ (δ=0.2 mm) along positive y-axis and no rotating about y-axis, z11 represents an operation of moving δ (δ=0.2 mm) along positive z-axis and rotating ω (ω=1° clockwise about z-axis;

(x33, y33, z33), x33 represents an operation of moving 3 (6=0.2 mm) along negative x-axis and rotating ω (ω=1° counterclockwise about x-axis, y33 represents an operation of moving δ (δ=0.2 mm) along negative y-axis and rotating ω (ω=1° counterclockwise about y-axis, z33 represents an operation of moving δ (δ=0.2 mm) along negative z-axis and rotating ω (ω=1° counterclockwise about z-axis.

For all teeth need to be repositioned, all possible combinations of operations are listed in Table 1.

TABLE 1

| Combination | Tooth 1 | Tooth 2 | Tooth 3 | ... | Tooth m |
|---|---|---|---|---|---|
| 1 | (x11, y11, z11) | (x11, y11, z11) | (x11, y11, z11) | ... | (x11, y11, z11) |
| ... | ... | ... | ... | ... | ... |
| 729 | (x33, y33, z33) | ... | ... | ... | ... |
| ... | (x11, y11, z11) | (x12, y11, z11) | (x11, y11, z11) | ... | (x11, y11, z11) |
| ... | ... | ... | ... | ... | ... |

TABLE 1-continued

| Combination | Tooth 1 | Tooth 2 | Tooth 3 | ... | Tooth m |
|---|---|---|---|---|---|
| 729$^m$ | (x33, y33, z33) | (x33, y33, z33) | (x33, y33, z33) | ... | (x33, y33, z33) |

In some embodiments, a general operator may be expressed by a 6 dimensional vector:

$$O=\{[dx,dy,dz,d\alpha,d\beta,d\gamma]|dx\in\{0,+1,-1\}\ldots\}$$

where dx, dy, and dz represent movement along x-axis, y-axis, and z-axis, respectively, dα, dβ, and dγ represent rotation about x-axis, y-axis, and z-axis, respectively.

A matrix M may be obtained:

$$M = \begin{bmatrix} 1 & -d\gamma & d\beta & 0 \\ d\gamma & 1 & -d\alpha & 0 \\ -d\beta & d\alpha & 1 & 0 \\ dx & dy & dz & 1 \end{bmatrix}$$

When an operator is applied on a tooth, the coordinate of a point on the tooth will be changed from [x, y, z, 1] into:

$$[x',y',z',1]=[x,y,z,1]*M \quad \text{equation (2)}$$

A user may select teeth need to be repositioned, may select operators for each tooth needs to be repositioned, may set limitation for each selected operator, and may set an order of tooth reposition, to narrow the state space, and thus to reduce computation load.

In one embodiment, a step of an operator may be set for two or more teeth independently. For example, a step of 0.2 mm may be set for an operator of moving along positive x-axis for tooth 1, and a step of 0.1 mm may be set for the operator of moving along positive x-axis for tooth 3.

In one embodiment, two or more limitations of an operator may be set for two or more teeth, respectively. For example, a limitation of 2 mm may be set for an operator of moving along positive x-axis for tooth 1, and a limitation of 1 mm may be set for the operator of moving along positive x-axis for tooth 3.

Figure 1:
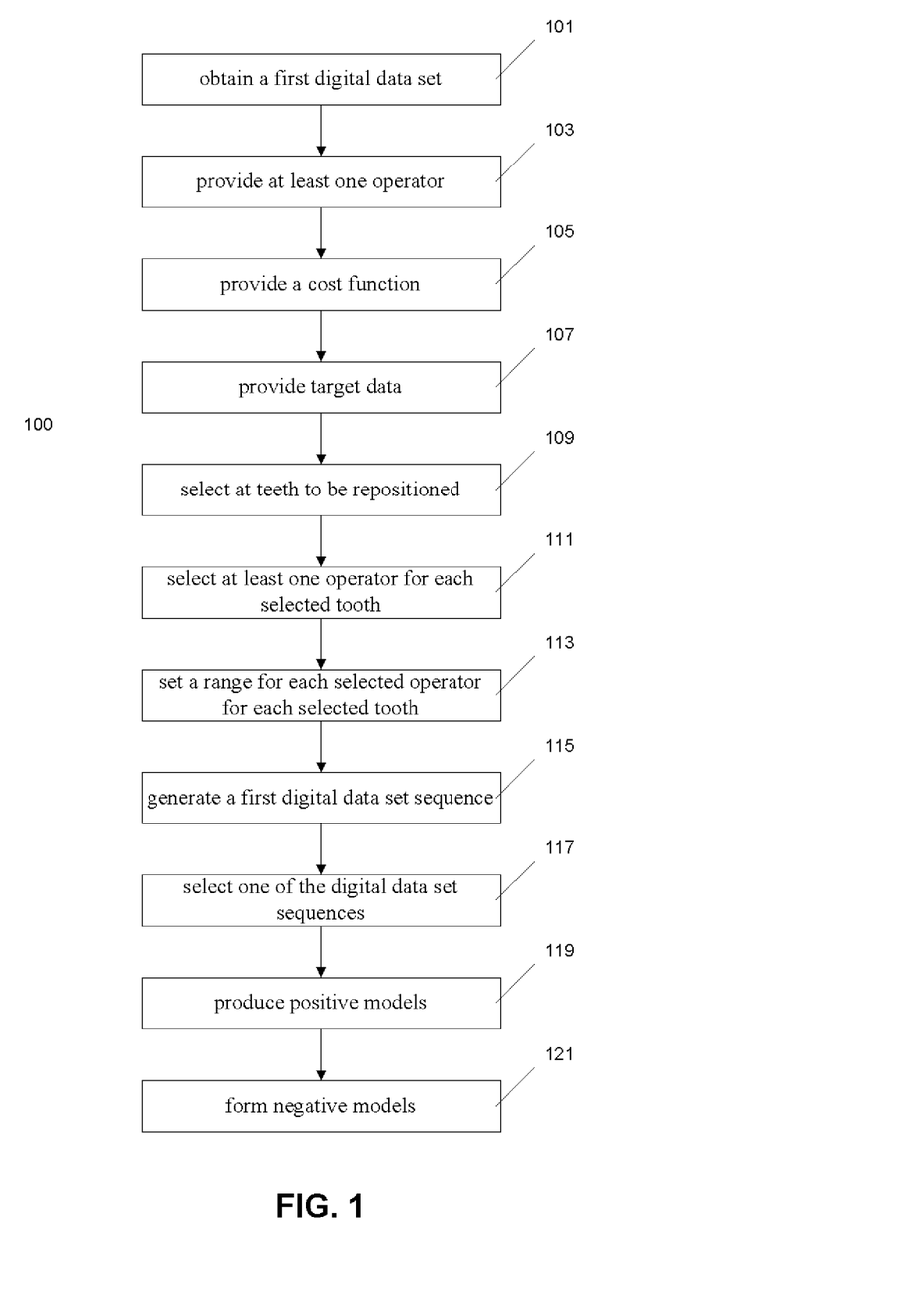
FIG. 1 illustrates a schematic flow chart of a method for manufacturing appliances for repositioning tooth using a heuristic state space search method according to one embodiment of the present application.

FIG. 1 illustrates a flow chart of a method 100 for manufacturing appliances for repositioning tooth using a heuristic state space search method. In 101, a first digital data set representing a first tooth arrangement is obtained. A digital data set digitally represents the 3D structure of a tooth arrangement. In one embodiment, a digital data set may include a plurality of digital data groups each of which may correspond to a tooth and may contain information such as contour and coordinate of the tooth. Those skilled in the art will appreciate that there are various data structures for a digital data set, and it will not be described in detail herein.

In 103, at least one operator is provided. An operator represents an operation such as movement, rotation, and interproximal enamel reduction etc. When an operator is applied on a tooth, the current digital data set will be modified. The modified digital data set represents a modified tooth arrangement which may be obtained by modifying the current tooth arrangement by applying the corresponding operation on the tooth.

In 105, a cost function is provided. The cost function includes at least one of the following parameters: the amount of crowding, overjet, overbite, dental arch convexity, depth of curve of Spec, Bolton ratio, dental arch width, arch symmetry, angulation of crown, tongue, and midline.

In 107, target data is provided as a criterion for determining whether a tooth arrangement meets the treatment requirements. In one embodiment, target data may include a predetermined ranges of selected parameters, e.g. 2~4 mm for overjet.

In 109, teeth need to be repositioned are selected according to user instructions to narrow the state space. A user or clinician may determine which tooth needs to be repositioned after observing a 3D image or a model of the current tooth arrangement.

In 111, at least one operator is selected for each selected tooth according to user instructions to narrow the state space. A user or clinician may determine for each selected tooth which operators are needed to reposition the tooth after observing a 3D image or a model of the current tooth arrangement.

In 113, a limitation is set for each selected operator for each selected tooth to narrow the state space. A user or clinician may determine the limitations after observing a 3D image or a model of the current tooth arrangement.

In 115, a first digital data set sequence having a plurality of successive digital data sets from a second digital data set to a $N^{th}$ digital data set is generated based on the first digital data set, the selected teeth, the selected operators, and the limitations, using a heuristic search method which is based on the cost function, where the $N^{th}$ digital data set represents a $N^{th}$ tooth arrangement which meets the treatment requirements. The first digital data set sequence represents a orthodontic treatment plan. In some embodiments, an order of tooth reposition may be determined before the search begins, to narrow the state space, thus to reduce computation load.

In some embodiments, the current digital data set may be compared with the previous digital data set to determine whether the current tooth arrangement is closer to the treatment requirements. If yes, the same operator may be applied on the same tooth continuously, if no, stop applying the operator on the tooth.

In some embodiments, each digital data set representing a tooth arrangement is generated based on a previous digital data set representing a previous tooth arrangement.

In 117, one of the digital data set sequences generated in 115 is selected as an orthodontic treatment plan according to user instructions. In some embodiments, a user or clinician may instruct to select the digital data set sequence according to the situation of the patient.

In 119, positive models of tooth arrangements are produced using the digital data set of the selected digital data set sequence. In some embodiments, the positive models may be produced by laser rapid prototyping technology.

In 121, negative models are formed on the positive models as appliances for repositioning tooth. Please refer to *The Vacuum Formed Dental Contour Appliance* by Henry I. Nahoum for a method of forming a negative model on a positive model of a tooth arrangement as an appliance for repositioning tooth.

In some embodiments, an OPEN table and a CLOSED table may be created. The OPEN table lists nodes to be explored, and the CLOSED table lists nodes that have been explored. In some embodiments, the OPEN table may be in form of table 2, and the CLOSED table may be in form of table 3.

TABLE 2

| Serial No. | Node | Operator | Cost Function Value |
|---|---|---|---|
| | | | |
| | | | |

TABLE 2-continued

| Serial No. | Node | Operator | Cost Function Value |
|---|---|---|---|
| | | | |

TABLE 3

| Serial No. | Node | Operator | Cost Function Value | Parent Node |
|---|---|---|---|---|
| | | | | |
| | | | | |
| | | | | |

Figure 2:
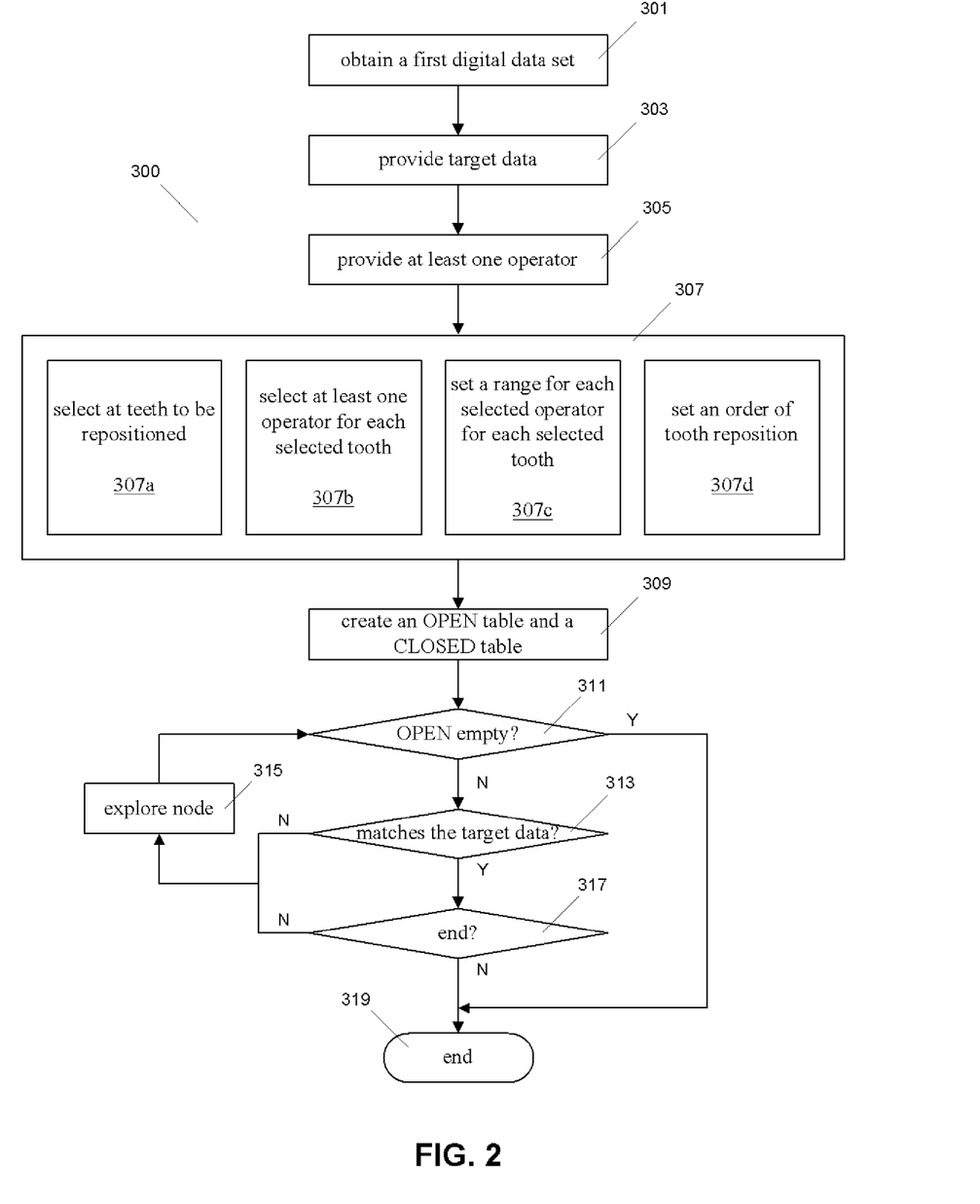
FIG. 2 illustrates a schematic flow chart of a method for manufacturing appliances for repositioning tooth using a state space search method according to one embodiment of the present application.

FIG. 2 illustrates a schematic flow chart of a method 300 for generating digital data sets using a state space search method according to one embodiment of the present application. The state space search method may be a blind search method. The method 300 includes at least one of the following:

in 301, obtaining a first digital data set representing a first tooth arrangement. In some embodiments, the first digital data set may be obtained from a compute readable medium. In some embodiments, the first digital data set may be obtained through a computer network;

in 303, providing target data according to user instructions. In one embodiment, target data may include predetermined ranges of selected parameters;

in 305, providing at least one operator for modifying digital data sets representing corresponding tooth arrangements;

in 307, selecting teeth need to be repositioned according to user instructions (307a), select at least one operator for each selected tooth according to user instructions (307b), set a limitation for each selected operator for each selected tooth according to user instructions (307c), and set an order of tooth reposition according to user instructions (307d);

in 307a, selecting in a jaw teeth need to be repositioned according to user instructions. By doing this, the unselected teeth may be kept stationary during the search to narrow the state space, and thus to improve the efficiency of the search;

in 307b, selecting at least one operator for each selected tooth according to user instructions. By doing this, for a tooth, the unselected operators may not be applied on the tooth to generate additional nodes to narrow the state space, and thus to improve the efficiency of the search;

in 307c, setting a limitation for each selected operator for each selected tooth according to user instructions. By doing this, the search may explore nodes within the limitation to narrow the state space, and thus to improve the efficiency of the search;

in 307d, setting an order of tooth reposition according to user instructions. For example, teeth 1, 2, and 3 may be repositioned synchronously first, and teeth 4, 5, and 6 may be repositioned synchronously thereafter. By doing this, many additional nodes may be reduced to narrow the state space, and thus to improve the efficiency of the search;

in 309, providing an OPEN table and a CLOSED table, and the OPEN table contains the first digital data set;

in 311, checking whether the OPEN table is empty, if no, go to 313, if yes which means that there is no solution, go to 319;

in 313, checking whether there is any digital data set in the OPEN table that meets the treatment requirements represented by the target data. If there is no such digital data set, go to 315, if there is such digital data set, go to 317. In some embodiments, if a digital data set that matches the target data is found, output a digital data set sequence having a plurality of digital data sets from the first digital data set to the digital data set that matches the target data. The digital data set sequence represents an orthodontic treatment plan;

in 315, moving a current digital data set from the OPEN table into the CLOSED table, and apply operators on the current digital data set to generate next level digital data sets, and the new generated nodes will be put in the OPEN table;

in 317, checking whether or not to end the search, if receive a user instruction of ending the search, go to 319, if receive a user instruction of continuing the search, go to 315; and in 319, ending the search.

Example 1

Figure 3:
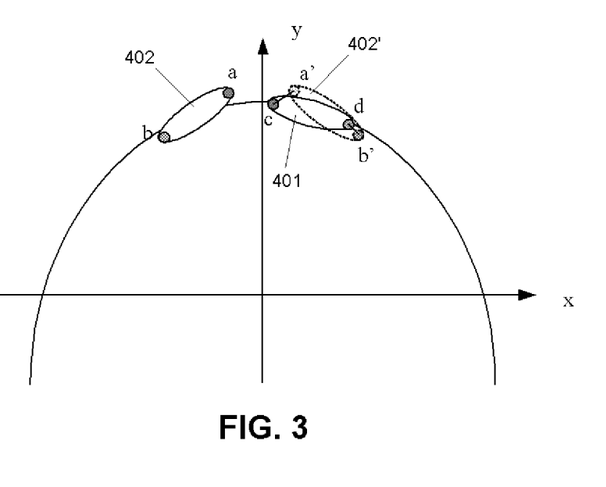
FIG. 3 illustrates a schematic bottom view of upper incisors of a first patient.

FIG. 3 illustrates a schematic bottom view of the upper incisors 401 and 402 of a first patient, where the incisor 401 is normal, and the incisor 402 needs to rotate clockwise about z-axis, move along positive x-axis, and maybe move along y-axis.

In this case, target data may include arch symmetry. In one embodiment, two reference points a and b are designated on the incisor 402, and two reference points c and d corresponding to the reference points a and b are designated on the incisor 401. The incisor 402 is mapped about y-axis to obtain a virtual incisor 402' and its reference points a' and b'. The sum of the length of the lines a'c and b'd is used as a measure of arch symmetry, the smaller the value, the higher the symmetry. In one embodiment, a threshold of 0.5 mm is given, as long as the sum is less than 0.5 mm, the tooth arrangement meets the treatment requirements.

Example 2

Figure 4A:
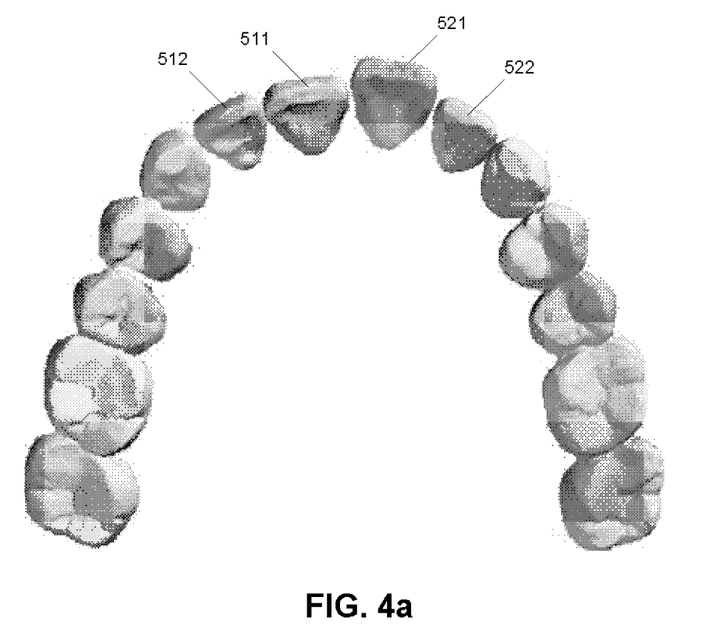
FIG. 4a illustrates a bottom view of the upper jaw of a second patient.
Figure 4B:
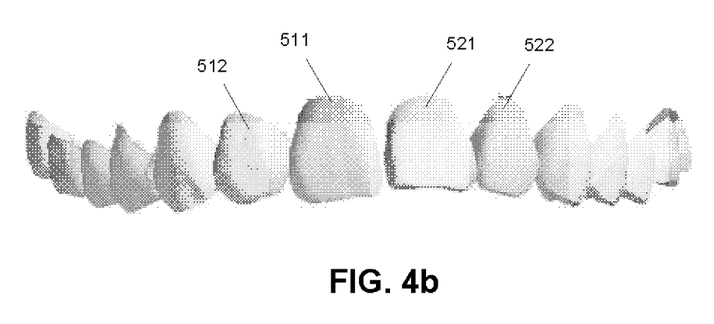
FIG. 4b illustrates a front view of the upper jaw of the second patient.
Figure 4C:
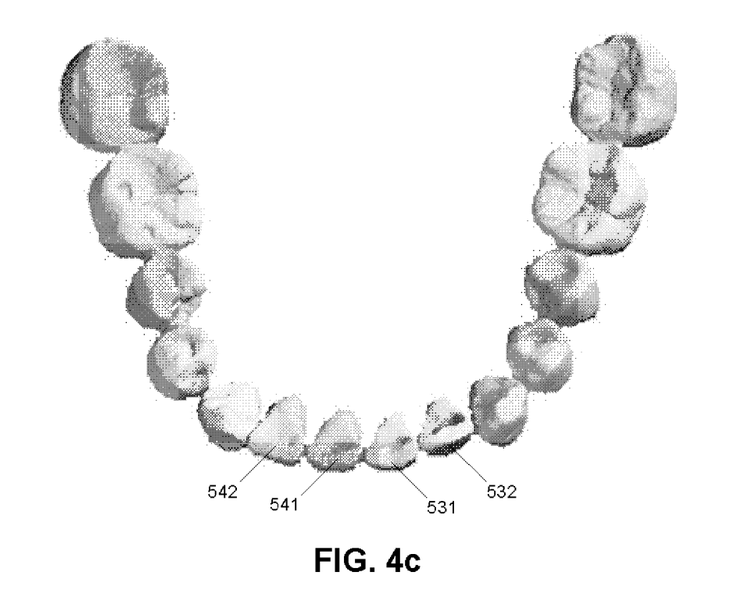
FIG. 4c illustrates a top view of the lower jaw of the second patient.
Figure 4D:
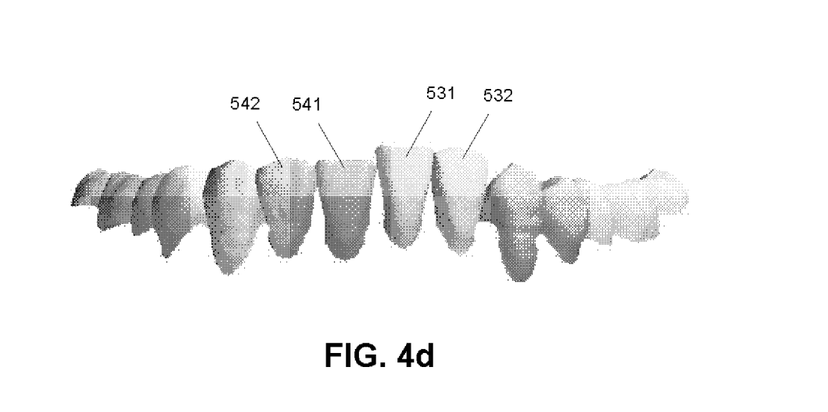
FIG. 4d illustrates a front view of the lower jaw of the second patient.

FIG. 4a illustrates a bottom view of the upper jaw of a second patient, FIG. 4b illustrates a front view of the upper jaw of the second patient, FIG. 4c illustrates a top view of the lower jaw of the second patient, and FIG. 4d illustrates a front view of the lower jaw of the second patient.

In this case, tooth 521 is inclined labially, and there is deep overbite. Tooth 511 is in normal position. There are enough space between the tooth 511 and tooth 522 to align the tooth 521. A treatment plan is to correct the tooth 521 by lingual inclination and translation, correcting crown angulation, and intruding. Tooth 531 and tooth 532 are intruded at the same time to correct deep overbite, to allow the movement of the tooth 521.

The tooth 511 may be used as a reference for the tooth 521, and target data may include parameters of overjet, overbite, tongue, angulation of crown, and the distance between incisor edge and occlusal plane etc.

For the tooth 531 and the tooth 532, tooth 541 and tooth 542 may be used as references correspondingly, and target data may include parameters of overbite, and the distance between incisor edge and occlusal plane etc.

Figure 5:
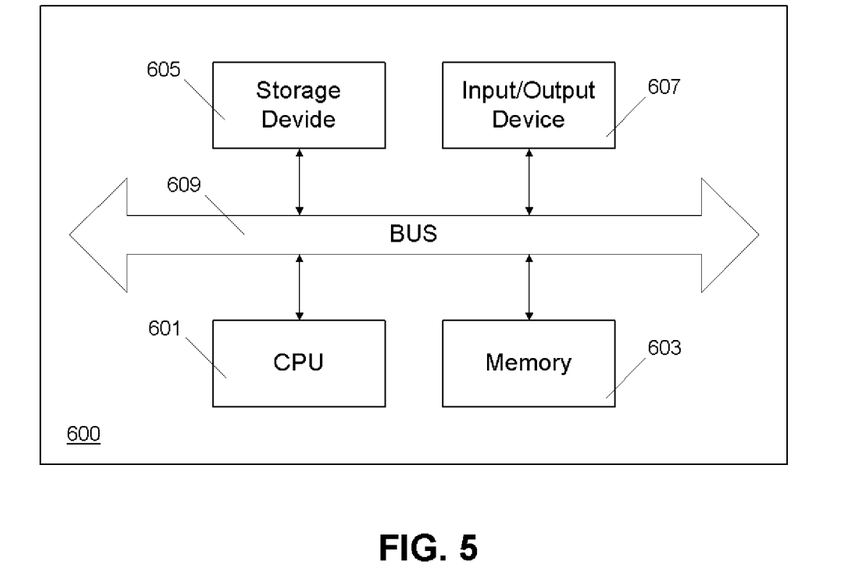
FIG. 5 illustrates a schematic block diagram of a computer system for generating digital data sets according to one embodiment of the present application.

FIG. 5 illustrates a schematic block diagram of a computer system 600 for generating digital data sets. The computer system 600 includes a processor 601, a memory 603, a storage device 605, and an input/output device 607 connected together through a BUS 609.

The storage device 605 has a computer program stored thereon (not shown) which program when executed by the processor 601 will instruct the processor 601 to conduct the parts involving generating digital data sets of the method 100 or the method 300.

The input/output device 607 may include a keyboard, a mouse, a display, and various input/output interfaces such as network interfaces, USB interfaces, IEEE1394 interfaces, E-SATA interfaces etc.

While various embodiments of the disclosed method and apparatus have been described above, it should be understood that they have been presented by way of example only, and not of limitation. Likewise, the various diagrams may depict an example architectural or other configuration for the disclosed method and apparatus, which is done to aid in understanding the features and functionality that can be included in the disclosed method and apparatus. The claimed invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the disclosed method and apparatus. Also, a multitude of different constituent module names other than those depicted herein can be applied to the various partitions. Additionally, with regard to flow diagrams, operational descriptions and method claims, the order in which the blocks are presented herein shall not mandate that various embodiments be implemented to perform the recited functionality in the same order unless the context dictates otherwise.

Although the disclosed method and apparatus is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed method and apparatus, whether or not such embodiments are described and whether or not such features are presented as being a part of a described embodiment. Thus, the breadth and scope of the claimed invention should not be limited by any of the above-described embodiments which are presented as mere examples for illustration only.

We claim:

1. A method for manufacturing an appliance for repositioning tooth, the method comprising:
    obtaining a first digital data set representing a first tooth arrangement;
    providing at least one operator for modifying the first digital data set;
    providing a heuristic search method based on a cost function, wherein the cost function contains an actual cost and an estimated cost;
    generating a second digital data set based on the heuristic search method using the first digital data set and the at least one operator, wherein the second digital data set represents a second tooth arrangement;
    providing orthodontic treatment requirements;
    determining whether the second tooth arrangement meets the orthodontic treatment requirements;
    producing a positive model of the second tooth arrangement when the second tooth arrangement meets the orthodontic treatment requirement;
    forming a negative model based on the positive model as the appliance for repositioning tooth;
    generating a $N^{th}$ digital data set representing a $N^{th}$ tooth arrangement based on the heuristic search method using a $N-1^{th}$ digital data set representing a $N-1^{th}$ tooth arrangement and the at least one operator if the $N-1^{th}$ tooth arrangement does not meet the orthodontic treatment requirement, wherein N is an integer greater than 2;
    determining whether the $N^{th}$ tooth arrangement meets the orthodontic treatment requirements;
    forming a first digital data set sequence having a plurality of successive digital data sets from the second digital data set to the $N^{th}$ digital data set if the $N^{th}$ tooth arrangement meets the orthodontic treatment requirement;
    producing a series of successive positive models of a corresponding series of successive tooth arrangements using the first digital data set sequence;
    forming a series of successive negative models based on the series of successive positive models as a series of successive appliances for repositioning tooth; and
    manufacturing a plurality of appliances using the $N^{th}$ digital data set.

2. The method of claim 1 further comprising: selecting in the first tooth arrangement at least one tooth needs to be repositioned.

3. The method of claim 2 further comprising: selecting at least one operator for said at least one selected tooth.

4. The method of claim 3 further comprising: setting a limitation for said at least one selected operator for said at least one selected tooth.

5. The method of claim 1 further comprising: setting a step for said at least one operator.

6. The method of claim 1, wherein the actual cost function or the estimated cost function comprises a parameter selected from the group consisting of the amount of crowding, overjet, overbite, dental arch convexity, depth of curve of Spee, Bolton ratio, dental arch width, arch symmetry, angulation of crown, tongue, midline and a combination thereof.

7. The method of claim 1, wherein said at least one operator is selected from the group consisting of movement along positive x-axis, movement along negative x-axis, movement along positive y-axis, movement along negative y-axis, movement along positive z-axis, movement along negative z-axis, clockwise rotation about x-axis, counterclockwise rotation about x-axis, clockwise rotation about y-axis, counterclockwise rotation about y-axis, clockwise rotation about z-axis, counterclockwise rotation about z-axis, and a combination thereof.

8. The method of claim 7, wherein a step of a movement operator is set in a range of 0.05~2 mm, and a step of a rotation operator is set in a range of 0.05~5°.

* * * * *